(12) United States Patent
Clark et al.

(10) Patent No.: US 7,942,837 B2
(45) Date of Patent: May 17, 2011

(54) COMPOSITE MOLDABLE SPLINT AND METHOD OF FORMING SAME

(75) Inventors: Gabriel Clark, Columbus, OH (US); Josef Otto, Lebanon, OH (US)

(73) Assignee: Prosthotics Functional Systems, LLC, Lebanon, OH (US)

( * ) Notice: Subject to any disclaimer, the term of this patent is extended or adjusted under 35 U.S.C. 154(b) by 322 days.

(21) Appl. No.: 12/105,476

(22) Filed: Apr. 18, 2008

(65) Prior Publication Data

US 2008/0262400 A1 Oct. 23, 2008

Related U.S. Application Data

(60) Provisional application No. 60/925,543, filed on Apr. 21, 2007.

(51) Int. Cl.
*A61F 5/00* (2006.01)
(52) U.S. Cl. ................ 602/6; 602/5; 602/7
(58) Field of Classification Search ........... 602/5–8, 602/20–22; 128/869, 882
See application file for complete search history.

(56) References Cited

U.S. PATENT DOCUMENTS

| | | | |
|---|---|---|---|
| 5,036,838 A | 8/1991 | Sherman | |
| 5,540,876 A | 7/1996 | Larson et al. | |
| 5,926,843 A | 7/1999 | Winchester | |
| 6,093,161 A | 7/2000 | Vlaeyen et al. | |
| 6,110,134 A | 8/2000 | Clark, Jr. et al. | |
| 6,129,695 A * | 10/2000 | Peters et al. | 602/62 |
| 6,358,220 B1 | 3/2002 | Langen et al. | |
| 2003/0171703 A1* | 9/2003 | Grim et al. | 601/152 |
| 2006/0086004 A1* | 4/2006 | Davis et al. | 36/43 |
| 2007/0136926 A1* | 6/2007 | Johnson et al. | 2/159 |
| 2008/0249446 A1* | 10/2008 | Baumgartner et al. | 602/7 |

* cited by examiner

*Primary Examiner* — Kim M Lewis (74) *Attorney, Agent, or Firm* — Gallagher & Dawsey Co., LPA; Michael J. Gallagher; David J. Dawsey (57) ABSTRACT

A composite moldable splint having at least a first splinting member with an inner foam layer, an intermediate thermoplastic layer, and an external securing layer. The inner foam layer provides a soft, moisture transmitting, non-latex padding. The intermediate thermoplastic layer provides remoldable shape, and rigidity and strength after heat forming and cooling. The outer securing layer, preferably covered with continuous loop fabric suitable for hook and loop fastening, provides an essentially infinite plurality of attachment points for retaining straps including at least a section of hook fastening material for holding the splint in place. The layers of the composite moldable splint are preferably heat welded to form a strong unitary structure that is resistant to delamination. Composite moldable splints utilizing multiple splinting members are described.

25 Claims, 11 Drawing Sheets

COMPOSITE MOLDABLE SPLINT AND METHOD OF FORMING SAME

RELATED APPLICATIONS

This application claims the benefit of U.S. provisional patent application Ser. No. 60/925,543; filed Apr. 21, 2007.

TECHNICAL FIELD

The instant invention relates to a composite moldable splint suitable for immobilization and support during neuromusculoskeletal tissue healing and rehabilitation.

BACKGROUND OF THE INVENTION

In the field of human and veterinary medicine, orthopedic splinting devices are formed to provide immobilization and support during neuromusculoskeletal tissue healing and rehabilitation. Traditional splinting techniques use a variety of materials including plaster, premolded polymers, and thermoplastic polymers. With the advent of custom formable thermoplastic synthetic materials, plaster is rarely used for conditions other than bone fractures. Thermoplastic splinting material can be heated and custom molded to the body part being treated. This method of splint fabrication conserves time and improves fit when compared to plaster casting.

Thermoplastic material is available in sheet stock and can be cut to the desired shape and size required for treatment. Following a 3-5 minute water bath between 100 and 200 degrees Fahrenheit, the thermoplastic is rendered pliable and easily molded to the body part to be treated. Although the duration of its pliability is relatively brief, the material can still be shaped and trimmed depending on its thickness and degree of heat exposure. As the thermoplastic cools to room temperature, it regains its original rigid nature and sustains the shape of the custom formed splint. Cooling can be expedited via cold compresses, water, and aerosol coolants specifically designed for splint fabrication.

In the field of rehabilitation, the art of splinting has expanded from basic immobilization and protection of injured structures to various dynamic applications. These applications include immobilization, therapeutic exercise, and neuromuscular reeducation. This new composite of the instant invention now affords dynamic splint designs that are adaptive in nature as well as restorative in regards to functional use. Examples of use include, by way of example and not limitation, a compensatory device to allow wrist and finger extension for peripheral or central nervous system disorders, dynamic traction of arthritic deforming forces in the hand while maintaining use, or as dynamic ankle-foot orthoses that facilitate a normalized gait pattern.

SUMMARY OF INVENTION

In its most general configuration, the present invention advances the state of the art with a variety of new capabilities and overcomes many of the shortcomings of prior devices in new and novel ways. In its most general sense, the present invention overcomes the shortcomings and limitations of the prior art in any of a number of generally effective configurations. The instant invention demonstrates such capabilities and overcomes many of the shortcomings of prior methods in new and novel ways.

A composite moldable splint includes at least a first splinting member. While embodiments including one and two splinting members are also described, there is no absolute restriction on the number of splinting members that may be used, nor any necessary relationship among the sizes and positions of multiple splinting members. The first splinting member further includes a plurality of layers; including a first foam layer, a first thermoplastic layer and a first securing layer.

These layers are bonded together, and the composite moldable splint is employed with the first foam layer nearest the intended user's skin, the first securing layer on the outside of the splint, and the thermoplastic layer lying between these two other layers. While the layers may be adhesively, or otherwise attached to one another, a preferred embodiment creates a heat weld, or fusion zone, between the layers that gives a strong unitary structure that is highly resistant to delamination. The first foam layer, preferably an elastomeric open-cell non-latex foam, provides a padded, moisture transmitting, non-migrating surface for user comfort. While many suitable elastomeric, non-migrating materials that are bondable to thermoplastic would be recognized by one skilled in the art; good results have been obtained using FABRI-FOAM™ from Fabrifoam Products of Exton, Pa. Further, in a preferred embodiment, the first thermoplastic layer of the composite moldable splint further includes a thermoplastic pliable at temperatures between about 100 to 200 degrees Fahrenheit; and good results have been achieved using a gamma radiation cross-linked thermoplastic polymer including at least in part, poly (epsilon-caprolactone).

The outside securing layer may be formed of any suitable material, as would be known to one skilled in the art, for covering the thermoplastic layer from the environment. In a preferred embodiment, the first securing layer has at least one section of loop fabric fastening on the first securing layer outer surface. In a preferred embodiment, the loop fabric covers at least 95% of the first securing layer surface area. This full, or substantially full coverage of the first securing layer outer surface with loop fabric fastening material confers important advantages. Retaining straps including at least a portion of a hook fastening material may be positioned at essentially any point on the first securing layer outside surface. Thus, different geometries in fastening may be employed by one skilled in the art to both secure the composite moldable splint and to create different force vectors applied by the composite moldable splint to the intended user.

The composite moldable splint may be perforated to promote moisture transfer through the composite moldable splint, and composite moldable splints utilizing more than a single splinting member are discussed.

Assembly of the composite moldable splint of the instant invention begins with assembling sheets of material for the first foam layer, the first thermoplastic layer, and the first securing layer; and then, in a preferred embodiment, heat welding these layers to form a unitary bonded splint assembly. After the bonded splint assemblies have cooled, a plurality of perforations communicating from the first securing layer outer surface to the first foam layer inner surface of the bonded splint assembly are punched in the bonded splint assemblies.

Next, a technician would cut sections from the bonded splint assembly to size for physiologic use, and then warm one or more of the cut sections for application to an intended user. Gentle manual pressure and manipulation may be used to form a physiologically conforming bonded splint assembly on the body of an intended user, taking into account the individual characteristics of the intended user and the purpose for the splinting. The warmed bonded splint assembly remains elastic and pliable for several minutes at room temperature, generally long enough for one skilled in the art to form a physiologically conforming bonded splint assembly, but the material may be returned to the water bath, or other heat source, at any time to restore elasticity and prolong working time.

When the technician is satisfied with the final shape and fit of the physiologically conforming bonded splint assembly, the composite moldable splint is cooled and completed by releasably securing the physiologically conforming bonded splint assembly with at least one retaining strap releasably attached to the first securing layer outer surface.

In a preferred embodiment, the first securing layer outer surface is substantially covered by a continuous loop fabric suitable for hook and loop fastening. One or more retaining straps that utilize hook fastening material may be placed and secured at virtually any aspect of the securing layer outer surface of a splint covered with continuous loop fabric. This allows the technician to vary the intensity and force vectors of any retaining straps applied.

The instant invention enables a significant advance in the state of the art. The instant invention is, in addition, widely applicable to a large number of applications. The various embodiments, as would be understood by one skilled in the art, would be suitable to any application requiring splinting of various types. These variations, modifications, alternatives, and alterations of the various preferred embodiments may be used alone or in combination with one another, as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures, all shown not-to-scale:

These drawings are provided to assist in the understanding of the exemplary embodiments of the invention as described in more detail below and should not be construed as unduly limiting the invention. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The composite moldable splint of the instant invention enables a significant advance in the state of the art. The preferred embodiments of the device accomplish this by new and novel arrangements of elements and methods that are configured in unique and novel ways and which demonstrate previously unavailable but preferred and desirable capabilities. The detailed description set forth below in connection with the drawings is intended merely as a description of the present embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 1:
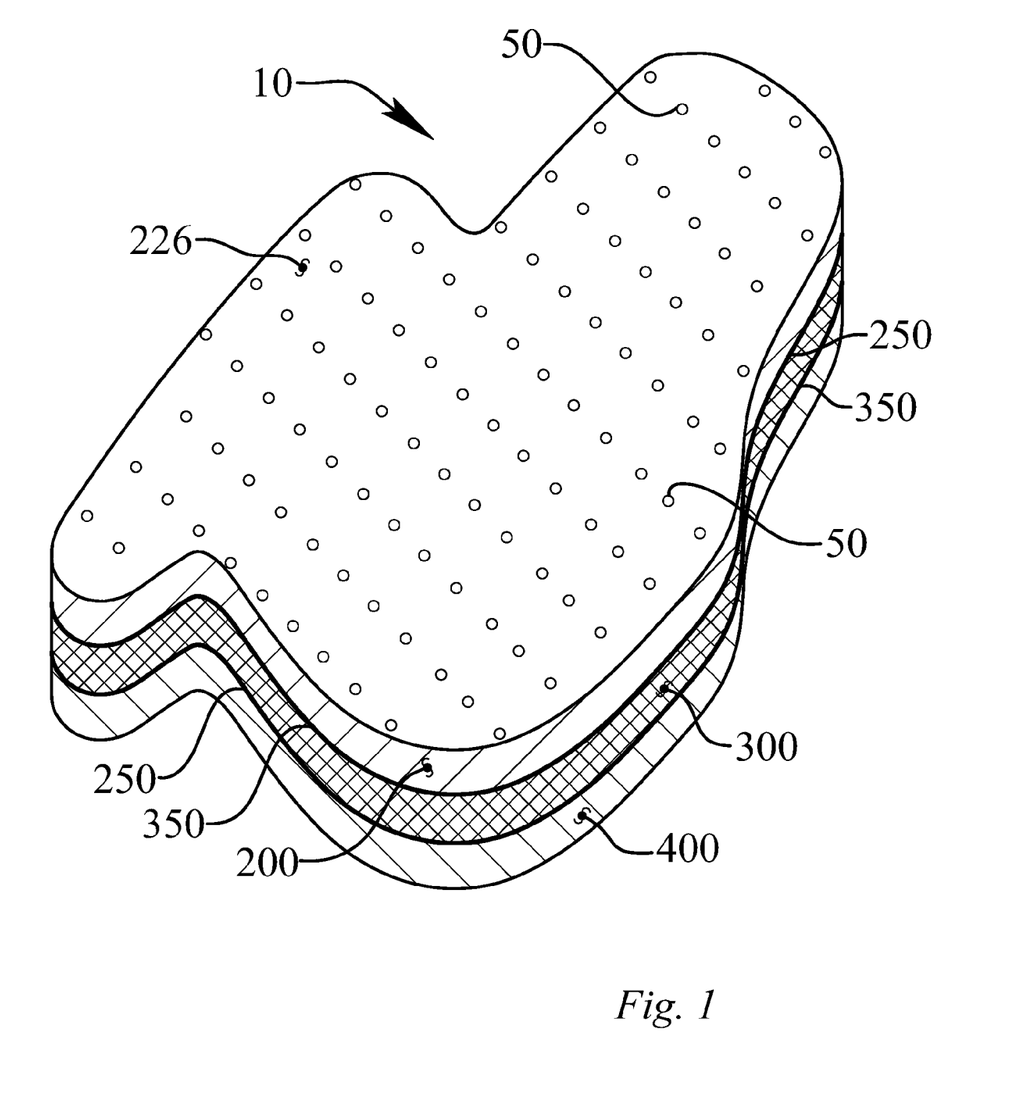
FIG. 1 is an elevated perspective drawing of an embodiment of the instant invention.

With regards to FIGS. 1-15, a composite moldable splint (10) is disclosed that includes at least a first splinting member (20), as seen well in FIG. 1. While embodiments including one and two splinting members (20, 30) are described, there is no absolute restriction on the number of splinting members (20, 30) that may be used, nor any necessary relationship among the sizes and positions of multiple splinting members (20, 30). The first splinting member (20) further includes a plurality of layers, as seen well in FIGS. 1-3. These layers will be described in part using the following conventions: aspects of the layers are indicated as "inner" if they are more proximal, or closer, to the skin of an intended user than those aspects identified as "outer," which are more distal, or farther, from the skin of an intended user. Additionally, as seen well in FIGS. 6, 8 and 15-16, applications are described in which the composite moldable splint (10) of the instant invention includes a first splinting member (20) and a second splinting member (30); and one skilled in the art will be able to envision applications using even further splinting members (20, 30). The descriptors "first" and "second" are not meant to imply that the structures or compounds described as such are the same or different from each other. While any structure or compound described herein as a "first" may equally be formed in the same manner as a "second" structure or compound; one skilled in the art may envision applications where the "first" and "second" (or additional) compounds and structures are preferably the same, or equally, applications where they are preferably different.

Figure 2:
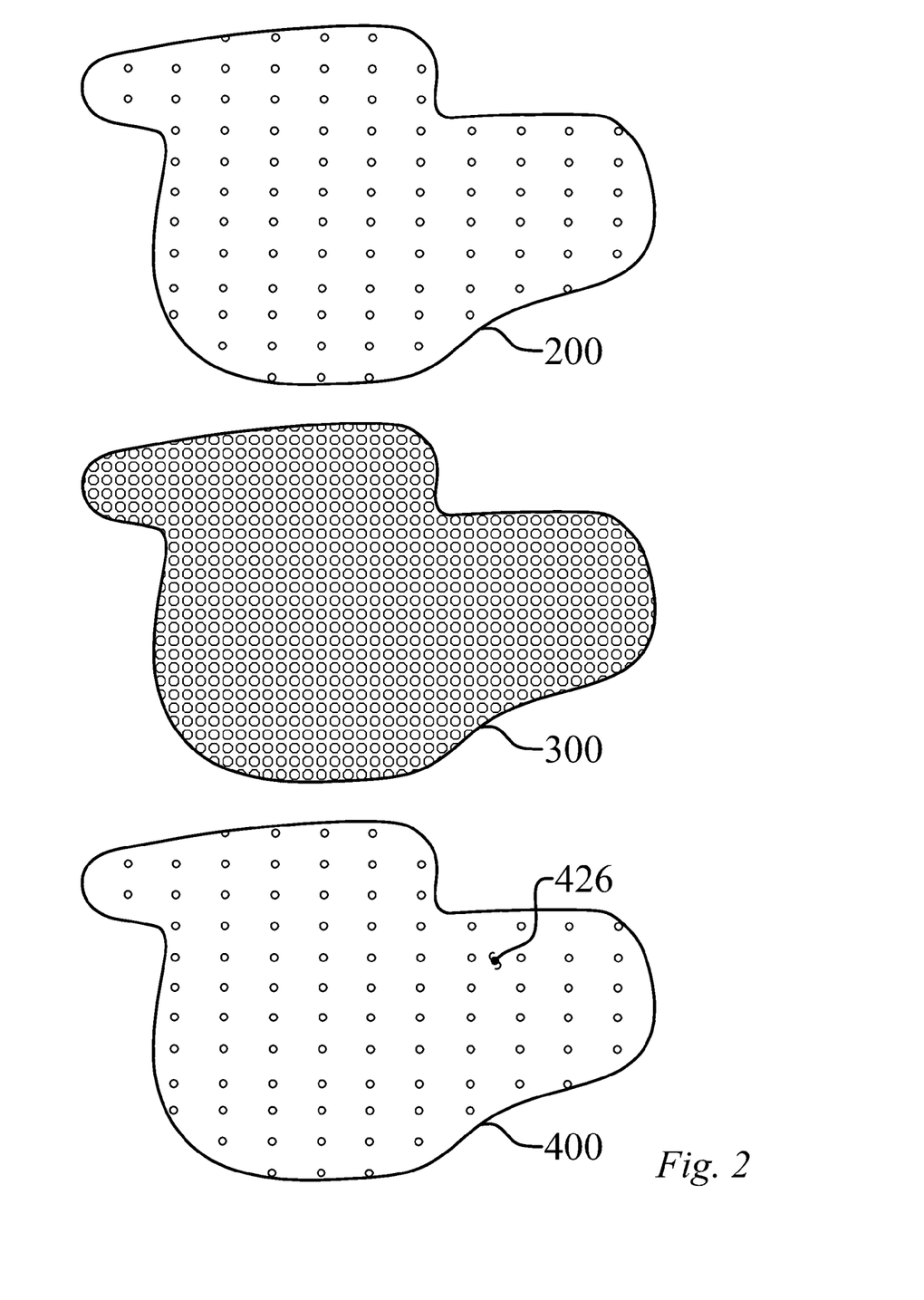
FIG. 2 is top plan drawing of a first foam layer, a first thermoplastic layer, and a first securing layer of the embodiment of FIG. 1.
Figure 3:
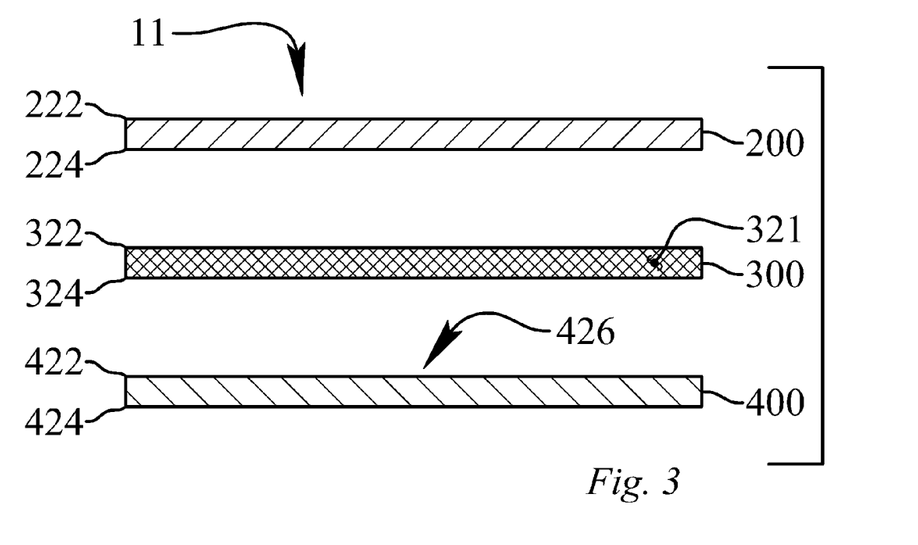
FIG. 3 is an exploded side view of the embodiment of FIG. 1, showing the relationship between layers in a first splinting member of the instant invention.

Therefore, as seen in FIGS. 1-3, the composite moldable splint (10) has a first foam layer (400) having at least a first foam layer outer surface (422), a first foam layer inner surface (424), and a first foam layer surface area (426). In keeping with the naming convention just discussed, the first foam layer inner surface area (424) is that aspect of the first foam layer (400) closest to the intended user's skin, while the first foam layer outer surface (422) is that aspect of the first foam layer (400) most distant from the intended user's skin.

Moving outwards, or away from, the intended user's skin, and as seen well in FIG. 3, the composite moldable splint (10) includes a first thermoplastic layer (300) having at least a first thermoplastic layer outer surface (322), a first thermoplastic layer inner surface (324) and a first thermoplastic layer surface area (326). Again, the first thermoplastic layer inner surface (324) is that aspect of the first thermoplastic layer (300) closest to the intended user's skin, while the first thermoplastic layer outer surface (322) is that aspect of the first thermoplastic layer (300) most distant from the intended user's skin. The first thermoplastic layer (300) has a first thermoplastic layer surface area (326) and the first thermoplastic layer (300) is positioned between and in contact with a first outer securing layer (200) and the first inner foam layer (400). This first securing layer (200) includes the outermost layer of the composite moldable splint and has at least a first securing layer outer surface (222), a first securing layer inner surface (224), and a first securing layer surface area (226).

Figure 5:
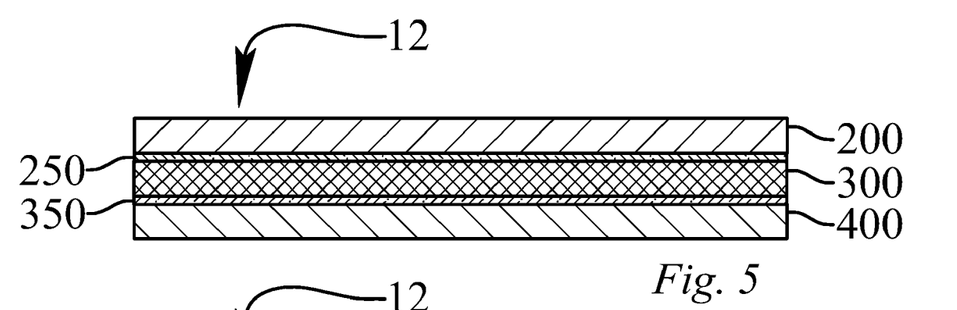
FIG. 5 is a side view of the embodiment of FIG. 1, showing a first foam layer, a first thermoplastic layer, and a first securing layer; after bonding, and demonstrating a first thermoplastic-securing layer bonding area and a first thermoplastic layer-foam bonding area.
Figure 7:
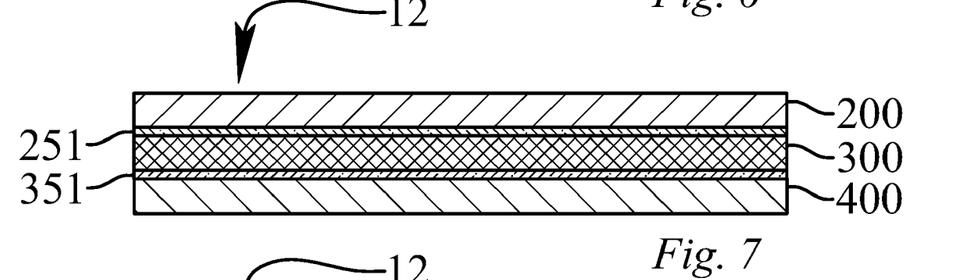
FIG. 7 is a side view of the embodiment of FIG. 1, showing a first foam layer, a first thermoplastic layer, and a first securing layer; after bonding, and demonstrating a first thermoplastic-securing layer fusion area and a first thermoplastic layer-foam fusion area.
Figure 8:
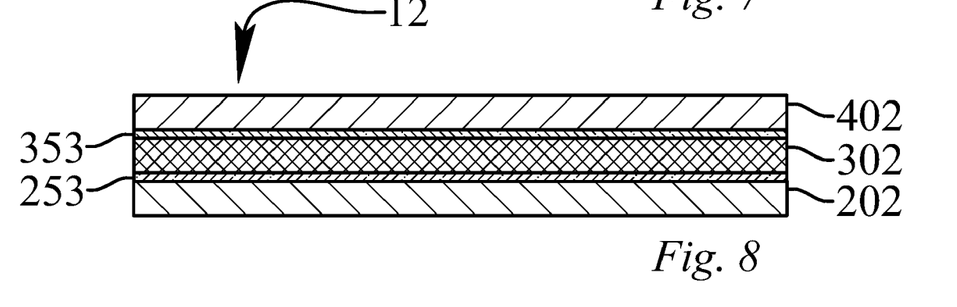
FIG. 8 is a side view of an embodiment of the instant invention, showing a second foam layer, a second thermoplastic layer, and a second securing layer; after bonding, and demonstrating a second thermoplastic-securing layer fusion area and a second thermoplastic layer-foam fusion area.
Figure 9:
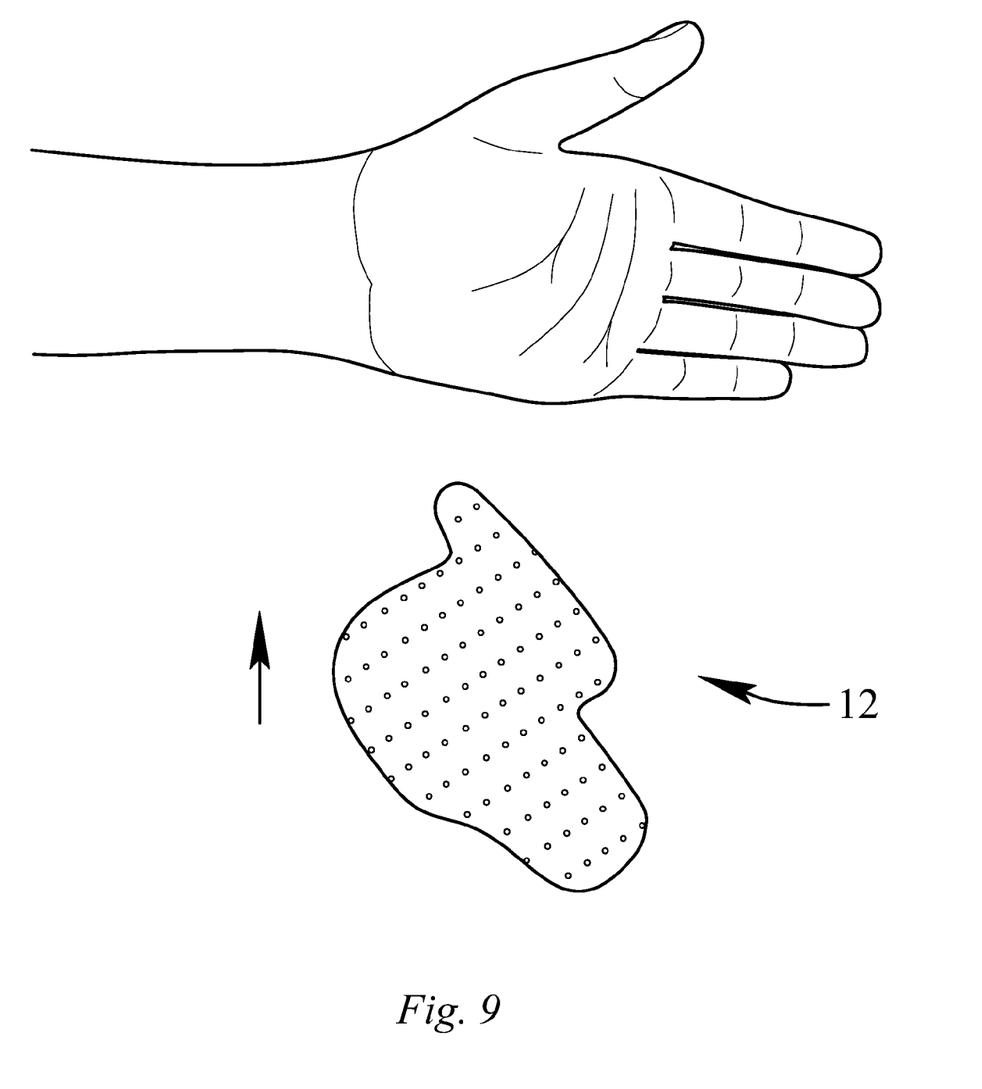
FIG. 9 is a top plan view showing an the embodiment of FIG. 1, ready for application to the palmar aspect of a human wrist and hand.

As may be seen in FIG. 5, the first thermoplastic layer inner surface (324) is bonded to the first foam layer outer surface (422) in a first thermoplastic-foam layer bonding area (350) and the first thermoplastic layer outer surface (322) is bonded to the first securing layer inner surface (224) in a first thermoplastic-securing layer bonding area (250). This bonding between the layers (200, 300, 400) gives the composite moldable splint (10) a laminated unitary structure that is highly resistant to delaminating. As seen in FIGS. 7-8, the bonding zones (250, 350) may be fusion zones (251, 351).

Figure 12:
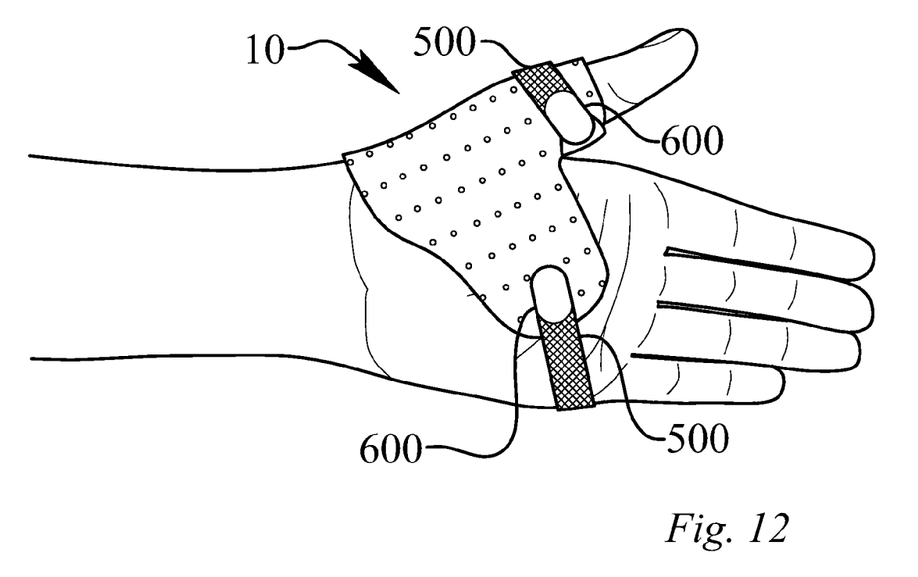
FIG. 12 is a top plan view of the embodiment of FIG. 1, showing final application of the instant invention to a palmar aspect of a human wrist and hand.
Figure 13:
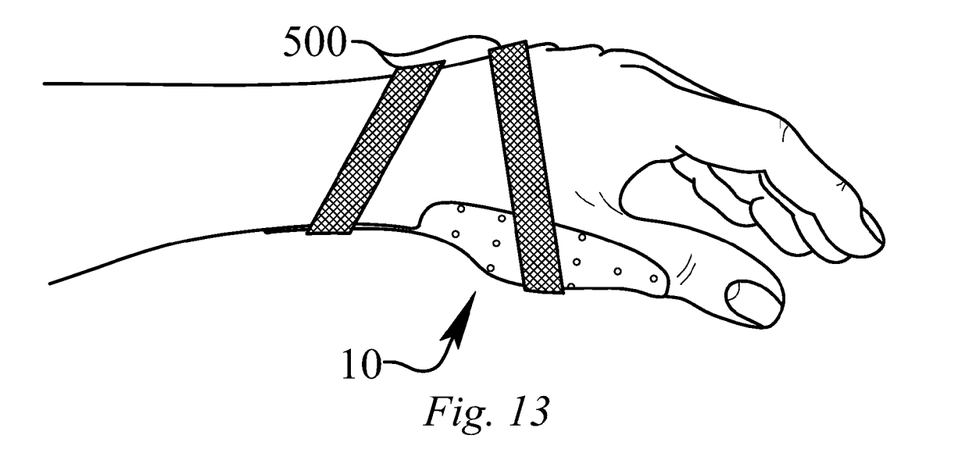
FIG. 13 is a side view of the embodiment of FIG. 1, showing final application of the instant invention to a palmar aspect of a human wrist and hand.
Figure 14:
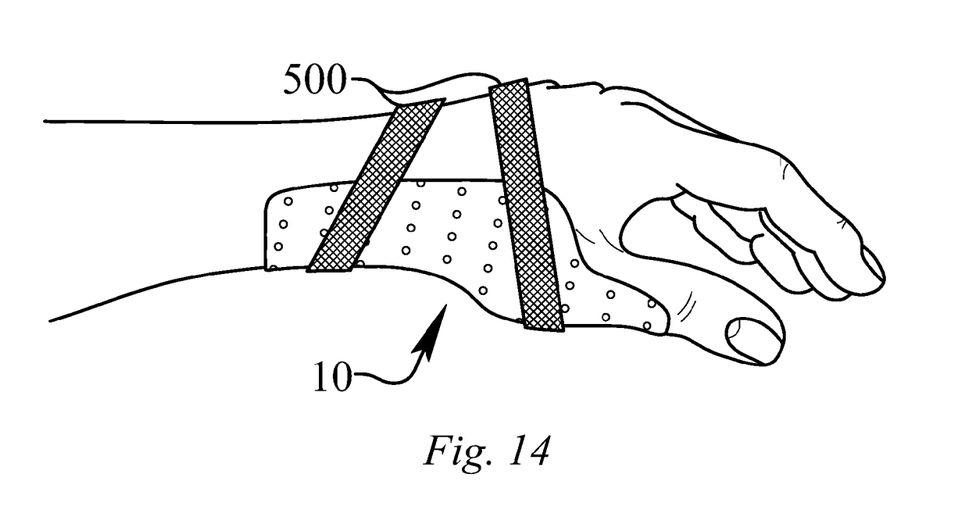
FIG. 14 is a side view of an alternative embodiment the instant invention, showing final application of the composite moldable splint to a palmar aspect of a human wrist and hand.

As seen well in FIGS. 12-14, the composite moldable splint (10) may be held in place by one or a plurality of retaining straps (500) releasably attached to the first securing layer outer surface (222). The mechanism and arrangement of the retaining straps (500) and their attachment to the securing layer (200) are a major advantage of the instant invention and will be discussed at length below.

Bonding between the first foam layer (400) and the first thermoplastic layer (300) in the first thermoplastic-foam layer bonding area (350) and bonding between the first thermoplastic layer (300) and the first securing layer (200) in the first thermoplastic-securing layer bonding area (250) may be accomplished in many ways, as would be known to one skilled in the art. These methods may include chemical fusion, adhesives, mechanical bonds, and fusion by heat or other radiation forms. In a preferred embodiment, the first thermoplastic-foam layer bonding area (350) further comprises a first thermoplastic-foam layer fusion zone (351), and the first thermoplastic-securing layer bonding area (250) further comprises a first thermoplastic-securing layer fusion zone (251). A preferred method of forming these fusion zones (251, 351) will be discussed below.

Various materials have been found advantageous in the formation of the composite moldable splint (10), and while only a few of these are discussed, one skilled in the art would recognize that a wide variety of materials are suitable for use.

In a preferred embodiment of the composite moldable splint (10) the first foam layer (400) includes an open cell foam, and in a further preferred embodiment the first foam layer (400) further includes a non-latex, open cell, foam.

An advantageous product for use in this layer is FABRIFOAM™ from Fabrifoam Products of Exton, Pa.; and certain embodiments of this material are described in U.S. Pat. No. 5,036,838.

FABRIFOAM® is a composite material combining an open-celled, elastomeric, non-latex foam that is applied to specifically engineered fabrics; these fabrics displaying a "four way stretch" capacity, that is, the ability to stretch in all dimensions. This allows the fabric backed foam to stretch, and thereby conform to compound curves without wrinkling. Further, as one skilled in the art would know, FABRIFOAM® is breathable and resists migration, which is the tendency of elastic materials to "creep" on the surface of skin during an intended user's body movement. The product also tends to wick away perspiration or other moisture, while the fabric surface is hook receptive to hook and loop fastening, such as that seen in various hook and loop fastening systems, such as by way of limitation only, VELCRO® from Velcro Industries, BV; of the Netherlands Antilles. However, any suitable elastomeric non-migrating material that is bondable to thermoplastic may be utilized in the first foam layer (400).

In an alternative embodiment, the first foam layer (400) is treated with an anti-microbial agent; which may include various silver compounds.

In a preferred embodiment, the first thermoplastic layer (300) of the composite moldable splint (10) further includes a thermoplastic pliable at temperatures between about 100 degrees and 200 degrees Fahrenheit. One skilled in the art will realize that the thermoplastic may be formed from the group of thermoplastics consisting of poly(ethyleneadipate), poly (epsilon-capronolactone), polyvinyl stearate, cellulose acetate, butyratre and ethyl cellulose poly(propylene oxide) containing monomers, trans polyisoprene, cis polyisoprene, polycapronolactone, and transpoly isoprene, among others.

In a preferred embodiment, an advantageous material for formation of the first thermoplastic layer (300) further includes a gamma radiation cross-linked thermoplastic polymer. A typically effective material formed at least in part of poly (epsilon-caprolactone) is disclosed in U.S. Pat. No. 5,540,876 to Larson. An effective commercial product for this application is the KLARITY™ splinting material available from Larson Medical Products, Inc. of Columbus, Ohio.

Figure 17:
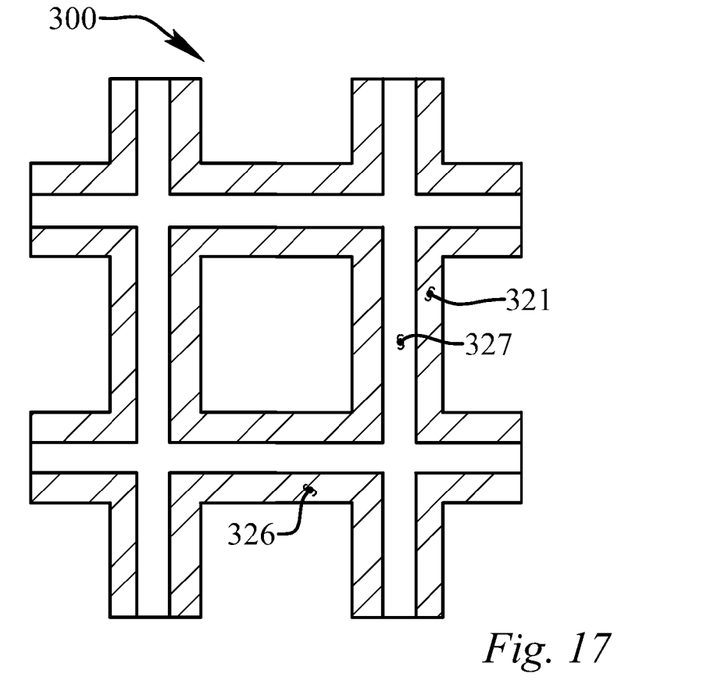
FIG. 17 is a detail of an embodiment of a first thermoplastic layer according to the instant invention.
Figure 18:
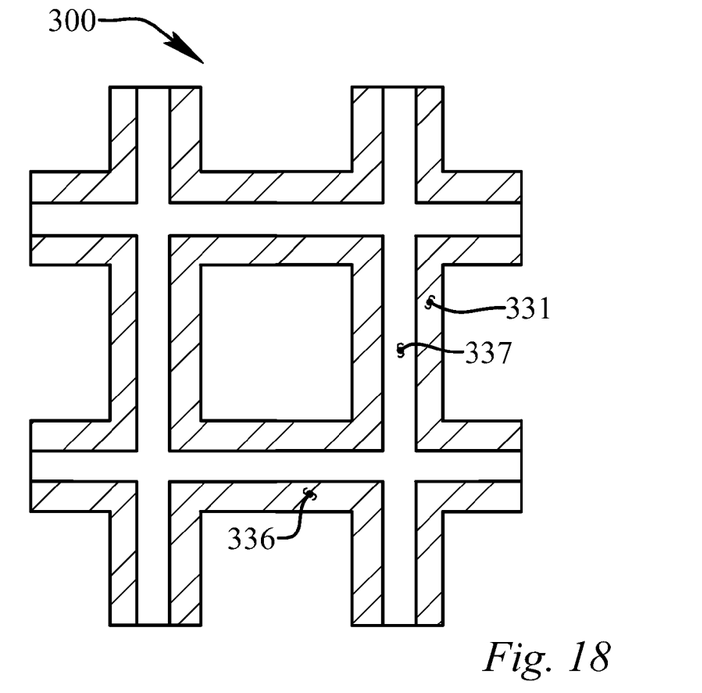
FIG. 18 is a detail of an embodiment of a second thermoplastic layer according to the instant invention.

In a preferred embodiment, seen in FIG. 17, the first thermoplastic layer is formed as a foraminous sheet, as illustrated in the teachings of Larson, having a first thermoplastic surface area (326). A first thermoplastic material (321) may be coated on a first netting (327), with the first thermoplastic material (321) coated around each strand. The utilization of a foraminous sheet structure lightens the overall weight of the composite moldable splint (10) and improves the transmission of moisture from the first foam layer outer surface (422) to the first securing layer inner surface (224). Comparable structure in a second thermoplastic layer (302) having a second thermoplastic surface area (336) are seen in FIG. 18, and include a second thermoplastic material (331) which may be coated on a second netting (337).

The securing layer seen well in FIG. 1 may be formed of any suitable material, as would be known to one skilled in the art, for covering the thermoplastic layer (300) from the environment. By way of example only, the securing layer may be a thermoplastic or a fabric. As seen well in FIG. 12-14, in one embodiment, the composite moldable splint (10) may be retained in place on an intended user by having at least one retaining strap (500) releasably secured to the first securing layer outer surface (222) with at least one attachment device (600) that is releasably attached to the at least one retaining strap (500) and the first securing layer outer surface (222). This attachment device (600) may be any form of fastener, and in a preferred embodiment, is at least a section of hook fastening designed to cooperate with at least one section of loop fabric fastening on the first securing layer outer surface (222). In a preferred embodiment, the loop fabric covers at least 95% of the first securing layer surface area (226).

This full, or substantially full coverage of the first securing layer outer surface (222) with loop fabric fastening material confers important advantages. Retaining straps (500) including at least a portion of a hook fastening material may be positioned at essentially any point on the first securing layer outside surface (222). Thus, different geometries in fastening may be employed by one skilled in the art to both secure the composite moldable splint (10) and to create different force vectors applied by the composite moldable splint (10) to the intended user.

In some embodiments, seen well in FIG. 1, it has been found advantageous to perforate the composite moldable splint (10) with a plurality of perforations (50) communicating between the first securing layer outer surface (222) and the first foam layer inner surface (424) of the splint. Such perforations (50) tend to promote moisture transfer through the composite moldable splint (10), and it has been found that a relatively small number of perforations (50) are suitable to accomplish this, and do not appreciably weaken the composite moldable splint (10). In some embodiments, the plurality of perforations (50) comprises a perforation surface area in total of less than 5% of the first securing layer surface area (226). In other preferred embodiments, the plurality of perforations (50) comprises a perforation surface area in total of less than 1% of the first securing layer surface area (226).

Figure 15:
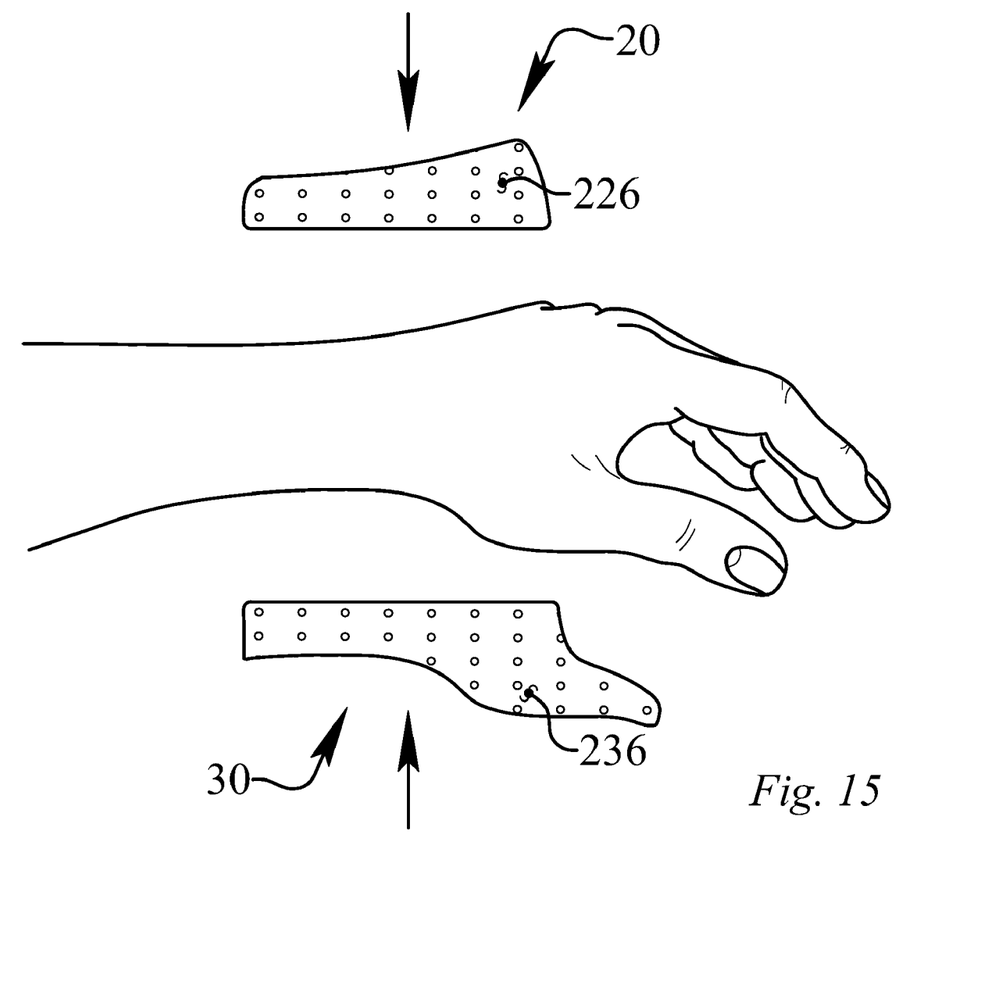
FIG. 15 is a side view of an alternative embodiment the instant invention, having a first splinting member and a second splinting member ready for final application to the palmar and dorsal aspects of a human wrist and hand.
Figure 16:
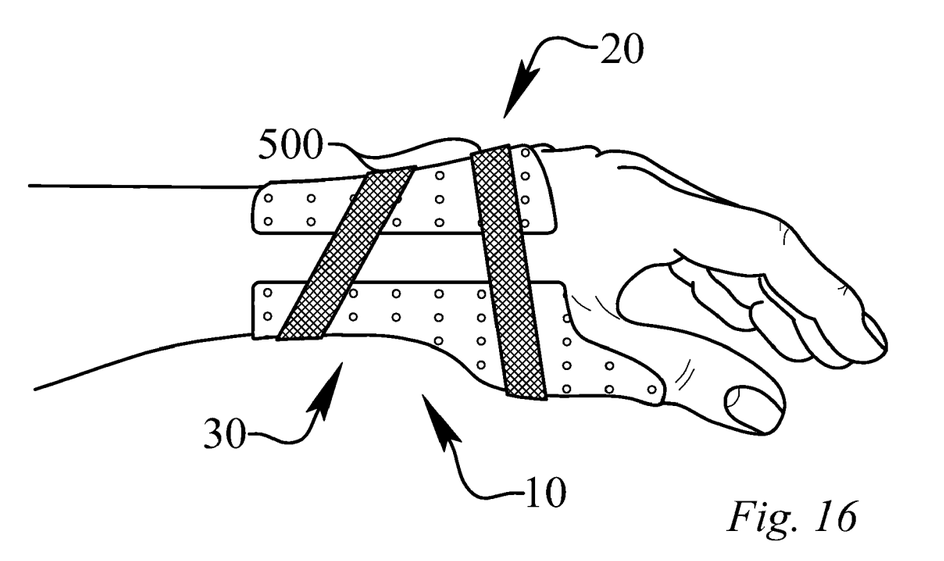
FIG. 16 is a side view of an alternative embodiment the instant invention, having a first splinting member and a second splinting member, shown in a final application position on the palmar and dorsal aspects of a human wrist and hand.

So far, this disclosure has only discussed a composite moldable splint (10) including a single, first splinting member (20). However, the instant invention is equally applicable to a composite moldable splint having a second (30), or even more than two, splinting members, as seen in FIG. 15-16.

In such embodiments, the first splinting member (20) and second splinting member (30) are most frequently at least partially opposing, although they may also be placed in a non-opposing manner, as would be understood by one skilled in the art. In such an embodiment, the second splinting member (30) is structurally the same as the first splinting member (20), as may be seen in FIGS. 5-8.

As seen well in FIG. 3, at least a first splinting member (20) includes a first securing layer (200) having at least a first securing layer outer surface (222), a first securing layer inner surface (224) and a first securing layer surface area (226). The first splinting member also has a first foam layer (400) having at least a first foam layer outer surface (422), a first foam layer inner surface (424) and a first foam layer surface area (426). The first splinting member also includes a first thermoplastic layer (300) having at least a first thermoplastic layer outer surface (322), a first thermoplastic layer inner surface (324) and a first thermoplastic layer surface area (326), where the first thermoplastic layer (300) is positioned between and in contact with the first securing layer (200) and the first foam layer (400).

In this embodiment as well, as may be seen in FIG. 5, the first thermoplastic layer inner surface (324) is bonded to the first foam layer outer surface (422) in a first thermoplastic-foam layer bonding area (350) and the first thermoplastic layer outer surface (322) is bonded to the first securing layer inner surface (224) in a first thermoplastic-securing layer bonding area (250).

Figure 4:
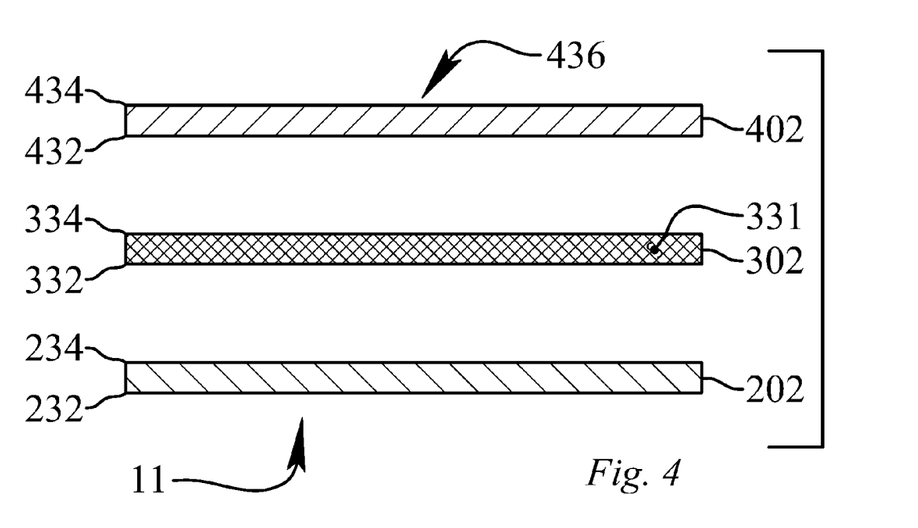
FIG. 4 is an exploded side view of the embodiment of FIG. 1, showing the relationship between layers in a second splinting member of the instant invention.

As seen well in FIG. 4, a second splinting member (30) has similar structure, that is, it includes a second securing layer (202) having at least a second securing layer outer surface (232), a second securing layer inner surface (234) and a second securing layer surface area (236). The second splinting member (30) also includes a second foam layer (402) having at least a second foam layer outer surface (432), a second foam layer inner surface (434) and a second foam layer surface area (436). And again, the second splinting member (30) has a second thermoplastic layer (302) having at least a second thermoplastic layer outer surface (332), a second thermoplastic layer inner surface (334) and a second thermoplastic layer surface area (336), the second thermoplastic layer (302) positioned between and in contact with the second securing layer (202) and the second foam layer (402).

Figure 6:
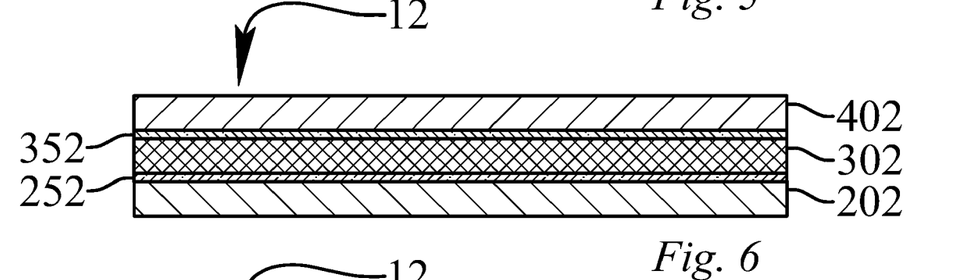
FIG. 6 is a side view of an embodiment of the instant invention, showing a second foam layer, a second thermoplastic layer, and a second securing layer; after bonding, and demonstrating a second thermoplastic-securing layer bonding area and a second thermoplastic layer-foam bonding area.

As with the structure of the first splinting member (20), in the second splinting member (30), seen well in FIG. 6, the second thermoplastic layer inner surface (334) is bonded to the second foam layer outer surface (432) in a second thermoplastic-foam layer bonding area (352) and the second thermoplastic layer outer surface (332) is bonded to the second securing layer inner surface (234) in a second thermoplastic-securing layer bonding area (252). In a preferred embodiment, seen well in FIGS. 7-8, the bonding areas (250, 252, 350, 352) may be fusion zones (251, 253, 351, 353).

The first splinting member (20) and the second splinting member (30), as well as any additional splinting members desired, are placed in physiologic position on an intended user, as seen well in FIGS. 15-16, and the at least first splinting member (20) is releasably attached to the at least second splinting member (30) by at least one retaining strap (500), seen in FIG. 16.

The composite moldable splint (10) of the instant invention may be fabricated according to a number of methods and technologies, which would be known to one skilled in the art, and only a few of which are discussed herein. No limitation as to possible methods of fabrication are expressed or intended.

In one embodiment of a method of fabrication, a method begins with assembling a splint assembly (11) for at least a first splinting member (20) having at least a first securing layer (200), a first thermoplastic layer (300), and a first foam layer (400).

Assembly may begin with a first securing layer (200) having at least a first securing layer outer surface (222), a first securing layer inner surface (224), and a first securing layer surface area (226). In a preferred embodiment, this first securing layer is a sheet of continuous loop fabric, suitable for hook and loop fastening, and approximately 18×24 inches in size.

Next, a first thermoplastic layer (300) of approximately the same size and having at least a first thermoplastic layer outer surface (322), a first thermoplastic layer inner surface (324) and a first thermoplastic layer surface area (326) is overlaid on the first securing layer (200). Then a first foam layer (400), again of approximately the same size, having at least a first foam layer outer surface (422), a first foam layer inner surface (424), and a first foam layer surface area (426) is overlaid on the first thermoplastic layer (300). One skilled in the art will realize that the order may be reversed, and a first foam layer (400) may be overlaid with a first thermoplastic layer (300) and then a first securing layer (200). Ultimately, it is only required that the first thermoplastic layer (300) be positioned between and in contact with the first securing layer (200) and the first inner foam layer (400). In those embodiments wherein the layers (200, 300, 400) of the splint assembly (11) are bonded by adhesive or the application of other substances to form a bonded splint assembly (12), it is necessary for these adhesives or other substances to be placed between the layers (200, 300, 400) during assembly of the layers (200, 300, 400).

However, in a preferred embodiment, a bonded splint assembly (12) is formed by applying heat or other energy to the splint assembly (11) thereby bonding the first thermoplastic layer inner surface (324) to the first foam layer outer surface (422) in a first thermoplastic-foam layer bonding area (350) and bonding the first thermoplastic layer outer surface (322) to the first securing layer inner surface (224) in a first thermoplastic-securing layer bonding area (250). Typically, heat welding is used to form the splint assembly (11) into the bonded splint assembly (12).

In a preferred and illustrative embodiment, the splint assembly (11), or plurality of splint assemblies (11) is placed in a VACUSEAL® 4468H Vacuum Press from Hunt Graphics Americas of Statesville, N.C. This is wide format laminator with a working capacity of 44"×68" that can easily accommodate four 18×24 inch splint assemblies (11) simultaneously. A typical processing protocol calls for an application of heat to 185-250 degrees Fahrenheit, along with 13 pounds per square inch (psi) pressure, for between five and seven minutes. Following heat welding, the bonded splint assemblies (12) are cooled on aluminum cooling tables under approximately twenty pounds of pressure to control the rate of heat dissipation and to prevent warping. One skilled in the art will realize that these parameters are variable according to material compositions and thicknesses, and other factors, and require adjustment for specific applications.

After the bonded splint assemblies have cooled, a plurality of perforations communicating from the first securing layer outer surface (222) to the first foam layer inner surface (424) of the bonded splint assembly (12) are punched in the bonded splint assemblies. In a preferred and illustrative embodiment, a CNC (Computer Numerically Controlled) turret punch press is used to perforate the sheets of bonded splint assemblies (12).

Next, one forming a splint who may for purposes of identification only be deemed a "technician," would cut sections from the bonded splint assembly (12) to size for physiologic use. These may range in size from quite small, possibly a square inch or smaller, to relatively large, possibly sufficient to cover a substantial part of a limb of an intended human or animal user. Hand shears can be used to cut the bonded splint assembly (12) and further trim it to approximate size and shape, according to the skill and experience of the technician.

To form a physiologically conforming splint assembly (13) the technician next warms the section of bonded splint assembly (12) to induce elasticity. In some embodiments, the bonded splint assembly (12) may be exposed to microwave energy or other energy source to induce elasticity. In a preferred embodiment, the section of bonded splint assembly (12) may be placed in a closed plastic bag and immersed in a water bath of approximately 100 to 200 degrees Fahrenheit, preferably about 170 degrees Fahrenheit, until elastic, typically about three to five minutes. While the bonded splint assembly (12), in a preferred embodiment, is not harmed by water, heating the bonded splint assembly (12) in a closed plastic bag helps keep the bonded splint assembly (12) dry and more comfortable for the intended user, as well as easier to work with for the technician.

Figure 10:
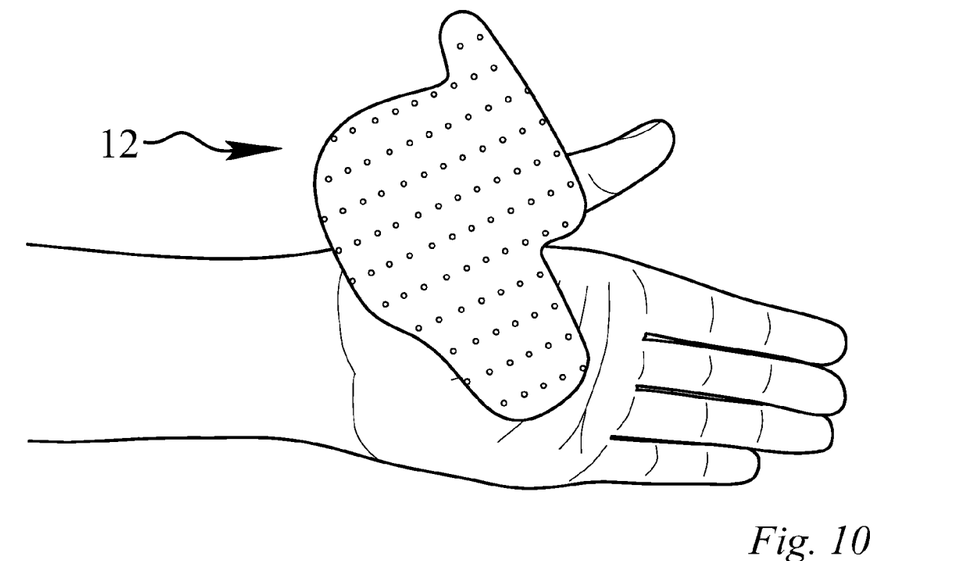
FIG. 10 is a top plan view showing the embodiment of FIG. 1, applied to the palmar aspect of a human wrist and hand, and ready for manipulation into final shape.
Figure 11:
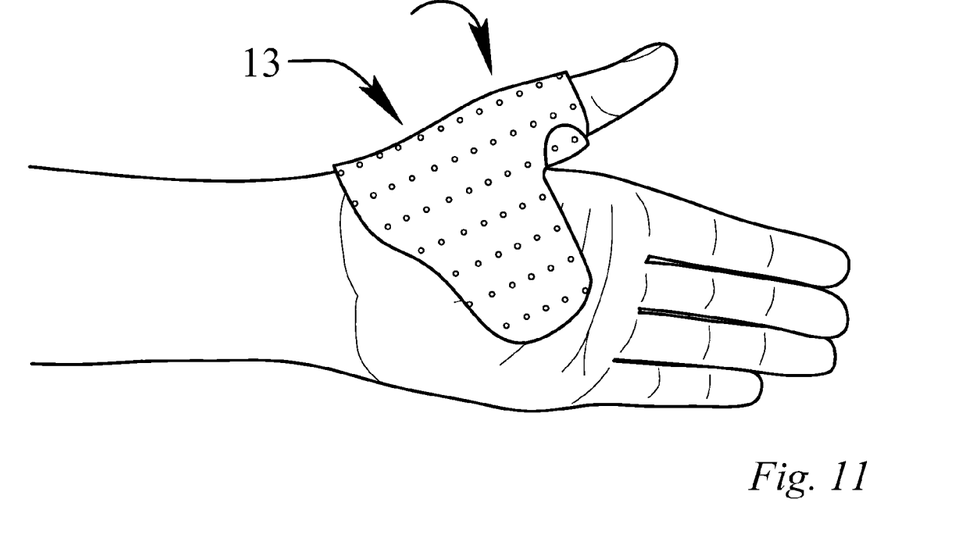
FIG. 11 is a top plan view showing the embodiment of FIG. 1, with directional arrows showing conformation of the instant invention to a palmar aspect of a human wrist and hand.

Next, the technician manipulates the warmed bonded splint assembly (12) to form a physiologically conforming bonded splint assembly (13) on the body of an intended user, as may be seen in FIGS. 10-11. Gentle manual pressure may be used to form the bonded splint assembly (12) into the correct shape, taking into account the individual characteristics of the intended user and the purpose for the splinting. The warmed bonded splint assembly remains elastic and pliable for several minutes at room temperature, generally long enough for one skilled in the art to form a physiologically conforming bonded splint assembly (13), but the material may be returned to the water bath, or other heat source, at any time to restore elasticity and prolong working time.

The physiologically conforming bonded splint assembly (13) may be allowed to cool in place on the intended user or may be removed once the technician ascertains that the level of elasticity has decreased sufficiently for the physiologically conforming bonded splint assembly (13) to hold its shape. Cooling can be expedited via cold compresses, cool water, and aerosol coolants specifically designed for splint fabrication. The physiologically conforming bonded splint assembly (13) is applied to the intended user and edges may be further trimmed with hand shears for final adjustment. Again, if the technician is unsatisfied with the shape of the physiologically conforming bonded splint assembly (13) at any time, it may be reheated to re-induce elasticity, and reworked.

When the technician is satisfied with the final shape and fit of the physiologically conforming bonded splint assembly (13), the composite moldable splint (10) is completed on the intended user by releasably securing the physiologically conforming bonded splint assembly (13) with at least one retaining strap (500) releasably attached to the first securing layer outer surface (222), as seen in FIGS. 12-14.

In a preferred embodiment, the first securing layer outer surface (222) is substantially covered by a continuous loop fabric suitable for hook and loop fastening. One skilled in the art will realize, as shown in FIGS. 12-14 and 16, that a retaining strap (500), or a plurality of retaining straps (500) that utilize hook fastening material, may be placed and secured at virtually any aspect of the securing layer outer surface (222). This allows the technician to vary the intensity and force vectors of any retaining straps (500) applied.

In a preferred embodiment, retaining straps are formed of FABIRFOAM® material bonded to a hook receptive fabric. Sections of hook material, which are seen in FIG. 12, for purposes of illustration only as disc-shaped, may then be used to affix the retaining straps (500), foam side against the intended user's skin, in virtually any desired direction and under a wide range of tensions. Alternatively, retaining straps (500) may be formed which incorporate sections of hook material affixed to the retaining straps (500), such that the hook-containing portion of the retaining straps (500) may cooperate with the continuous loop fabric on the first securing layer outer surface (222). It is, of course, to be remembered that the hook and loop fastening method discussed above is only one alternative that would be understood by one skilled in the art, and that many other methods may be used to secure the composite moldable splint (10) in place on an intended user.

One skilled in the art will also understand that for composite moldable splints (20) using a first splinting member (20) and a second splinting member (30), or additional splinting members (20, 20); similar fixation methods may be used. For example, as seen in FIGS. 15-16, an application using a generally opposing first splinting member (20) and a second splinting member (30) is shown; a retaining strap (500) such as that described above and incorporating a hook and loop fastening system may be attached by a first part to the first splinting member (20), tensioned as desired, and then attached by a second part to the second splinting member (30). This may be seen well in FIG. 16 and would form what might be deemed a "clam shell" splint that would splint an affected area from two sides.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only a few variations of the present invention are described herein, it is to be understood that the practice of such additional modifications and variations and the equivalents thereof, are within the spirit and scope of the invention as defined in the following claims. The corresponding structures, materials, acts, and equivalents of all means or step plus function elements in the claims below are intended to include any structure, material, or acts for performing the functions in combination with other claimed elements as specifically claimed.

We claim:

1. A composite moldable splint (10) comprising;
   at least a first splinting member (20) that when exposed to an energy source becomes pliable and capable of being directly applied to an intended user and manipulated to conform to the physiological characteristics of the intended user, the at least a first splinting member (20) having,
   a first securing layer (200) having at least a first securing layer outer surface (222), a first securing layer inner surface (224), and a first securing layer surface area (226), wherein the first securing layer (200) comprises a fabric;
   a first foam layer (400) having at least a first foam layer outer surface (422), a first foam layer inner surface (424), and a first foam layer surface area (426);
   a first thermoplastic layer (300) having at least a first thermoplastic layer outer surface (322), a first thermoplastic layer inner surface (324) and a first thermoplastic layer surface area (326), wherein the first thermoplastic layer (300) is coextensive with the first securing layer (200) and the first foam layer (400) and is positioned between and in contact with the first securing layer (200) and the first foam layer (400); and
   wherein the first thermoplastic layer inner surface (324) is bonded to the first foam layer outer surface (422) in a first thermoplastic-foam layer bonding area (350) and the first thermoplastic layer outer surface (322) is bonded to the first securing layer inner surface (224) in a first thermoplastic-securing layer bonding area (250).

2. The splint according to claim 1, further comprising at least one retaining strap (500) releasably attached to the first securing layer outer surface (222).

3. The splint according to claim 1, wherein the first thermoplastic-foam layer bonding area (350) further comprises a first thermoplastic-foam layer fusion zone (351).

4. The splint according to claim 1, wherein the first thermoplastic-securing layer bonding area (250) further comprises a first thermoplastic-securing layer fusion zone (251).

5. The splint according to claim 1, wherein the first thermoplastic-foam layer bonding area (350) and the first thermoplastic-securing layer bonding area (250) further comprise an adhesive.

6. The splint according to claim 1, wherein the first thermoplastic layer (300) further comprises a thermoplastic pliable at temperatures between about 38 degrees and 93 degrees Celsius.

7. The splint according to claim 1, wherein the first thermoplastic layer (300) further comprises a gamma radiation cross-linked thermoplastic polymer.

8. The splint according to claim 1, wherein the first thermoplastic layer further comprises a thermoplastic selected from the group of thermoplastics consisting of poly(ethylene-adipate), poly(epsilon-capronolactone), polyvinyl stearate, cellulose acetate, butyratre and ethyl cellulose poly(propylene oxide) containing monomers, trans polyisoprene, cis polyisoprene, polycapronolactone, and transpoly isoprene.

9. The splint according to claim 1, wherein the first foam layer (400) further comprises an open cell foam.

10. The splint according to claim 1, wherein the first foam layer (400) further comprises a non-latex foam.

11. The splint according to claim 1, wherein the first foam layer (400) is treated with an anti-microbial agent.

12. The splint according to claim 1, wherein the at least one retaining strap (500) is releasably secured to the first securing layer outer surface (222) with at least one attachment device (600) releasably attachable to the at least one retaining strap (500) and the first securing layer outer surface (222).

13. The splint according to claim 1, wherein the first splinting member (20) is perforated with a plurality of perforations communicating between the first securing layer outer surface (222) and the first foam layer inner surface (424) of the splint.

14. The device according to claim 13, wherein with the plurality of perforations comprises a perforation surface area in total of less than 5% of the first securing layer surface area (226).

15. The device according to claim 13, wherein with the plurality of perforations comprises a perforation surface area in total of less than 1% of the first securing layer surface area (226).

16. The splint according to claim 1, wherein the first securing layer outer surface (222) further comprises a hook and loop closure loop fabric.

17. The splint according to claim 16, wherein the loop fabric covers at least 95% of the first securing layer surface area (226).

18. The splint according to claim 16, wherein the loop fabric covers at least 50% of the first securing layer surface area (226).

19. A composite moldable splint (10), comprising,
   at least a first splinting member (20) that when exposed to an energy source becomes pliable and capable of being directly applied to an intended user and manipulated to conform to the physiological characteristics of the intended user, the at least a first splinting member (20) having, a first securing layer (200) having at least a first securing layer outer surface (222), a first securing layer inner surface (224) and a first securing layer surface area (226), wherein the first securing layer (200) comprises a fabric;

a first foam layer (400) having at least a first foam layer outer surface (422), a first foam layer inner surface (424) and a first foam layer surface area (426);

a first thermoplastic layer (300) having at least a first thermoplastic layer outer surface (322), a first thermoplastic layer inner surface (324) and a first thermoplastic layer surface area (326), the first thermoplastic layer (300) is coextensive with the first securing layer (200) and the first foam layer (400) and is positioned between and in contact with the first securing layer (200) and the first foam layer (400);

wherein the first thermoplastic layer inner surface (324) is bonded to the first foam layer outer surface (422) in a first thermoplastic-foam layer bonding area (350) and the first thermoplastic layer outer surface (322) is bonded to the first securing layer inner surface (224) in a first thermoplastic-securing layer bonding area (250); and at least a second splinting member (30) that when exposed to an energy source becomes pliable and capable of being directly applied to an intended user and manipulated to conform to the physiological characteristics of the intended user, the at least a second splinting member (30) having, a second securing layer (202) having at least a second securing layer outer surface (232), a second securing layer inner surface (234) and a second securing layer surface area (236), wherein the second securing layer (202) comprises a fabric;

a second foam layer (402) having at least a second foam layer outer surface (432), a second foam layer inner surface (434) and a second foam layer surface area (436);

a second thermoplastic layer (302) having at least a second thermoplastic layer outer surface (322), a second thermoplastic layer inner surface (324) and a second thermoplastic layer surface area (326), the second thermoplastic layer (302) positioned between and in contact with the second securing layer (202) and the second foam layer (402); and wherein the second thermoplastic layer inner surface (334) is bonded to the second foam layer outer surface (432) in a second thermoplastic-foam layer bonding area (352) and the second thermoplastic layer outer surface (332) is bonded to the second securing layer inner surface (234) in a second thermoplastic-securing layer bonding area (252).

20. The splint according to claim 19, wherein the at least first splinting member (20) is releasably attached to the at least second splinting member (30) by at least one retaining strap (500).

21. A method for forming a composite moldable splint (10) comprising the steps of;

assembling a splint assembly (11) for at least a first splinting member (20) having, a first securing layer (200) having at least a first securing layer outer surface (222), a first securing layer inner surface (224), and a first securing layer surface area (226), wherein the first securing layer (200) comprises a fabric;

a first foam layer (400) having at least a first foam layer outer surface (422), a first foam layer inner surface (424), and a first foam layer surface area (426);

a first thermoplastic layer (300) having at least a first thermoplastic layer outer surface (322), a first thermoplastic layer inner surface (324) and a first thermoplastic layer surface area (326), wherein the first thermoplastic layer (300) is coextensive with the first securing layer (200) and the first foam layer (400) and is positioned between and in contact with the first securing layer (200) and the first foam layer (400); and forming a bonded splint assembly (12) by bonding the first thermoplastic layer inner surface (324) to the first foam layer outer surface (422) in a first thermoplastic-foam layer bonding area (350) and bonding the first thermoplastic layer outer surface (322) to the first securing layer inner surface (224) in a first thermoplastic-securing layer bonding area (250).

22. The method according to claim 21, wherein the step of bonding the first thermoplastic layer inner surface (324) to the first foam layer outer surface (422) in a first thermoplastic-foam layer bonding area (350) and bonding the first thermoplastic layer outer surface (322) to the first securing layer inner surface (224) in a first thermoplastic-securing layer bonding area (250) further comprises the step of applying energy to the splint assembly (11) thereby forming a bonded splint assembly (12) by fusing the first thermoplastic layer inner surface (324) to the first foam layer outer surface (422) in a first thermoplastic-foam layer fusion area (351) and bonding the first thermoplastic layer outer surface (322) to the first securing layer inner surface (224) in a first thermoplastic-securing layer fusion area (251).

23. The method according to claim 21, further comprising the step of forming a plurality of perforations communicating from the first securing layer outer surface (222) to the first foam layer inner surface (424) of the bonded splint assembly (12).

24. The method according to claim 21, further comprising the steps of cutting the bonded splint assembly (12) to size for physiologic use;

warming the bonded splint assembly (12) to elasticity;

manipulating the warmed bonded splint assembly (12) to form a physiologically conforming bonded splint assembly (13) on the body of an intended user;

cooling the physiologically conforming bonded splint assembly (13); and applying the physiologically conforming bonded splint assembly (13) to an intended user.

25. The method according to claim 24, further comprising the step of completing the composite moldable splint (10) on the intended user by releasably securing the physiologically conforming bonded splint assembly (13) with at least one retaining strap (500) releasably attached to the first securing layer outer surface (222).

* * * * *